United States Patent [19]

Gaeke, deceased et al.

[11] Patent Number: 4,944,292
[45] Date of Patent: Jul. 31, 1990

[54] MOBILE RESUSCITATING APPARATUS

[75] Inventors: John C. Gaeke, deceased, late of Westlake, Ohio; by Louise Gaeke, executrix, 2245 Marshfield Blvd., Westlake, Ohio 44145

[73] Assignee: Louise M. Gaeke, Sequel, Calif.

[21] Appl. No.: 33,904

[22] Filed: Mar. 31, 1987

Related U.S. Application Data

[63] Continuation of Ser. No. 712,541, Mar. 15, 1985, abandoned.

[51] Int. Cl.⁵ .............................................. A61M 15/00
[52] U.S. Cl. ........................... 128/204.18; 128/205.24; 128/205.23; 248/122; 248/129; 137/343; 137/597; 137/883
[58] Field of Search ......................... 137/343, 597, 883; 128/204.18, 204.25, 205.24, 202.13, 205.23; 248/122, 129

[56] References Cited

U.S. PATENT DOCUMENTS

| | | | |
|---|---|---|---|
| 1,024,724 | 4/1912 | Gras | 248/122 |
| 1,977,725 | 10/1934 | Heidbrink . | |
| 2,039,901 | 5/1936 | Hawley . | |
| 2,042,474 | 6/1936 | McKesson . | |
| 2,162,242 | 6/1939 | Branower | 128/205.24 |
| 3,297,372 | 1/1967 | Brader . | |
| 3,377,856 | 4/1968 | Hasegawa | 73/199 |
| 3,743,122 | 7/1973 | Fortriede | 248/129 |
| 3,757,776 | 9/1973 | Bauman . | |
| 3,791,403 | 2/1974 | Folkerth | 128/204.18 |
| 3,838,687 | 10/1974 | Mosher . | |
| 4,020,834 | 5/1977 | Bird | 128/204.25 |
| 4,026,026 | 5/1977 | Richardson . | |
| 4,111,342 | 9/1978 | Kirby . | |
| 4,151,843 | 5/1979 | Brekke et al. . | |
| 4,160,323 | 7/1979 | Tracy . | |
| 4,187,845 | 2/1980 | Dror . | |
| 4,204,535 | 5/1980 | Pohlmann . | |
| 4,294,481 | 10/1981 | Pearl . | |
| 4,510,930 | 4/1985 | Garcia | 128/205.25 |

Primary Examiner—Carroll B. Dority
Attorney, Agent, or Firm—Watts, Hoffmann, Fisher & Heinke

[57] ABSTRACT

A mobile resuscitating apparatus with a detachable and portable oxygen delivery unit adapted to deliver either low or high pressure oxygen ventilation. A stand with casters supports the oxygen delivery unit for movement in the vicinity of a patient. Two oxygen canisters are coupled to flow control valves through a manifold. One valve regulates the volume of oxygen delivered to the patient and a second valve regulates oxygen pressure. The canisters, valves and manifold can be detached from the stand and carried with the patient to a medical facility. Two storage containers organize various drugs and airway maintenance equipment used in performing emergency resuscitation.

5 Claims, 5 Drawing Sheets

MOBILE RESUSCITATING APPARATUS

This is a continuation of co-pending application Ser. No. 712,541 filed on Mar. 15, 1985 and now abandoned.

DESCRIPTION

1. Technical Field

This invention relates to a mobile resuscitating apparatus and, in particular, it relates to a resuscitating apparatus with a portable oxygen delivery unit adapted to deliver either low or high pressure ventilation to a victim of respiratory difficulty.

2. Background Art

Medical emergencies involving respiratory difficulty or arrest may occur in environments where there are trained personnel who can, if the proper equipment is available, administer advanced first aid before the victim is transported to an emergency facility. Respiratory arrest may arise in physicians' offices or in out-patient surgery, and is relatively common in dentists' offices.

Some of the factors in respiratory difficulty or arrest are the medically compromised patient susceptible to a myocardial infarction or with congestive heart failure; the administration of drugs leading to anaphylaxis; the presence of foreign material in the airway; and stress. The last two factors are relatively frequent causes of breathing difficulties in the dentist's office.

Simple fainting or syncope, caused by stress and anxiety due to dental procedures, usually only requires that a victim's airway be maintained and that some oxygen be provided.

The victim of a myocardial infarction or congestive heart failure requires immediate oxygen administration and transport to an emergency facility. If the congestive heart failure is complicated by acute pulmonary edema, the victim requires high concentrations of oxygen to prevent or ease hypoxia during transport.

Anaphylactic shock due to allergic reactions to drugs may progress from manageable respiratory difficulty to laryngeal edema causing airway obstruction. A victim with laryngeal edema may require a tracheotomy so that his airway can be maintained for the administration of oxygen.

The chance of objects falling in the posterior of the pharynx exists during certain dental procedure. Usually, such an object is swallowed, but it can enter the trachea to cause acute airway obstruction. Total airway obstruction leads to unconsciousness in ten seconds and permanent neurologic damage in three to five minutes. Non-invasive techniques, such as the Heimlich maneuver, may not be successful in restoring the airway, so that an invasive technique, such as a tracheotomy is called for. Even after the tracheotomy, spontaneous respiration may not occur, so that the victim requires artificial ventilation through the tracheotomy.

The typical dentist office is ill-equiped to handle the spectrum of emergencies involving respiratory distress which may occur. Available emergency equipment usually consists of a small tank of oxygen capable of delivering one to ten liters per minute for thirty minutes and a mask or nasal prongs. The oxygen tank is awkward in transport, whether on a wheeled dolly or carried by hand. If the victim needs to be transported to an emergency facility, the tank is often placed on the stretcher between the victim's legs to keep it stationary.

An oxygen mask cannot be used with the unconscious patient without manual compression of a resuscitation bag. Nor does a mask suffice in the case of asphyxia due to aspirated matter unless a tracheotomy is performed. A tracheotomy is performed with a scalpel, with the incision being made large enough to accommodate an artificial airway should ventilation with a resuscitation bag be necessary.

Accessories, such as artificial airways and a self-inflating bag and mask for artificial ventilation, and drugs, such as epinephrine for anaphylaxis, are often stored away from the oxygen supply.

DISCLOSURE OF INVENTION

The present invention provides a mobile resuscitation apparatus well-suited for emergency situations arising away from acute medical care facilities. The resuscitation apparatus of the invention provides medical intervention options heretofore usually available only in the acute medical emergency care facilities of hospitals.

One feature of the invention is that it provides a mobile resuscitation apparatus having a portable oxygen delivery unit with a novel manifold design to give the operator a choice between low pressure or volume ventilation and high pressure or jet ventilation. The low pressure ventilation mode, providing oxygen at one to ten liters per minute is useful in medical emergencies when the victim remains conscious and cooperative, i.e., breathing on his own. The high pressure or jet ventilation mode, delivering oxygen up to one hundred psi, is indispensable in situations when the victim is uncooperative, i.e., unable to breathe on his own due to blockage in the trachea or respiratory arrest.

Another feature of the mobile resuscitation apparatus is that the portable oxygen delivery unit and manifold are designed to be easily transported by hand or on a stretcher to accompany the victim to a medical facility. The portable oxygen delivery unit and manifold mounted on a moveable stand for movement about the office or in the area of the victim and can be easily detached for movement with the patient.

The moveable stand has two pivoting supply containers. The container may be a tray or a case with latchable lid. These containers carry drugs and equipment organized for rapid access. The drugs may be in a packaged, commercially available kit, or the practitioner may design his own drug kit. The drug kit is stored in one container separate from the airway maintenance and resuscitation accessories all stored in the other container, preferably a latchable case. Both containers can be pivoted from a horizontal to vertical orientation so that the resuscitating apparatus takes minimum space when not in use.

From the above it is apparent that one object of the invention is a mobile resuscitating apparatus having a versatility unknown in the prior art. This and other objects, advantages and features of the invention will become better understood from a description of a preferred embodiment of the invention which is described in conjunction with the accompanying drawings.

BRIEF DESCRIPTION OF THE DRAWINGS

FIG. 3A is a view of a percutaneous transtracheal ventilation device.

BEST MODE FOR CARRYING OUT THE INVENTION

Figure 1:
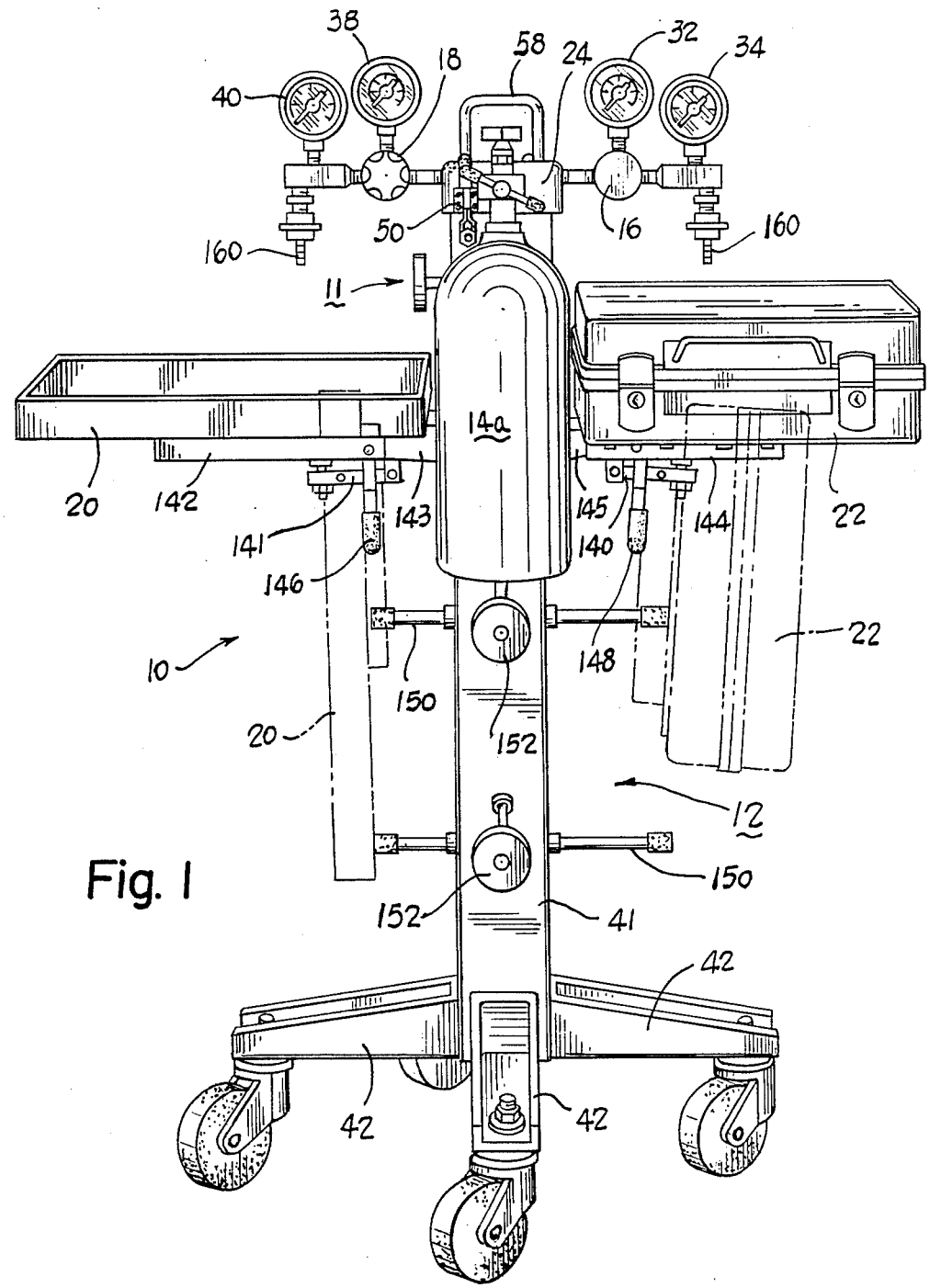
FIG. 1 is a perspective view of a mobile resuscitating apparatus supported on a moveable stand.

Referring to FIG. 1, a mobile resuscitating apparatus 10 comprises a portable oxygen delivery unit 11 mounted on a moveable stand 12. The portable oxygen delivery unit 11 includes two oxygen canisters 14a, 14b and oxygen regulators 16, 18 for delivering oxygen from the canisters 14a, 14b to a patient. Two storage containers 20, 22 mounted on the stand 12 carry drugs and airway management equipment used in ministering to a patient. A manifold 24 is provided to route oxygen from the two canisters 14a, 14b to an associated one of the oxygen regulators 16, 18. The first oxygen regulator 16 is adapted to deliver oxygen at low pressure for normal oxygen flow ventilation. The second oxygen regulator 18 is adapted to deliver oxygen at high pressure for high frequency or jet ventilation.

Figure 3:
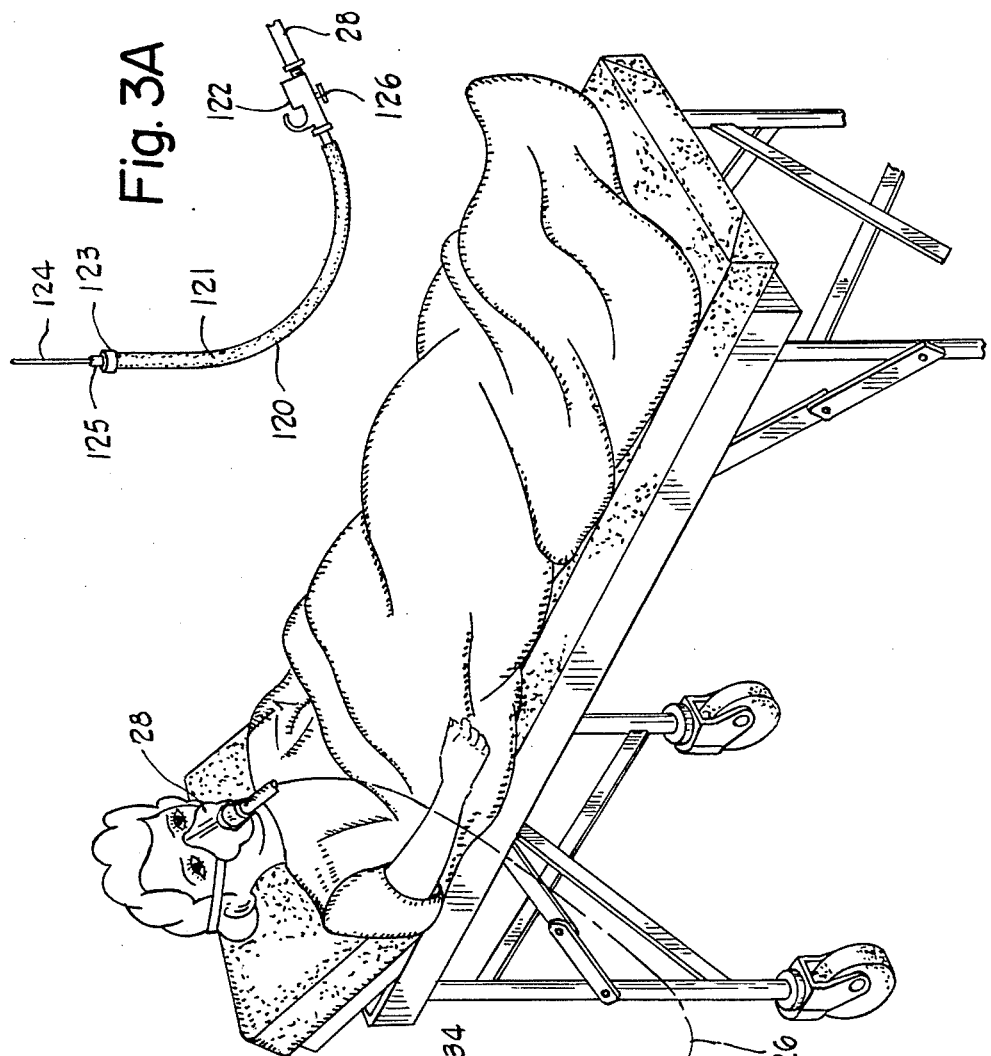
FIG. 3 is a perspective view showing the mobile resuscitating unit in use.

One feature of the invention is the versatility of the portable oxygen delivery unit 11. FIG. 3 shows the portable oxygen delivery unit 11 detached from the stand 12 and in use with a cooperative patient. Since the patient is able to breathe on his own, oxygen is supplied at low pressure to an oxygen mask 28 through a flexible tube 26 from the first oxygen regulator 16. The regulator 16 regulates oxygen flow via an adjustable handle 30. A first gauge 32 indicates the pressure from the oxygen canister 14a. The flow rate of oxygen to the patient is indicated in volume per unit time by a second gauge 34.

If the patient is unable to breathe on his own, or if it is otherwise medically indicated, the operator may deliver oxygen to the patient at high pressure for jet ventilation. FIG. 3A illustrates a jet ventilation device 120 adapted for transtracheal ventilation. Transtracheal ventilation is both an alternative to a tracheotomy performed with a scalpel and a preliminary intervention before a subsequent tracheotomy. Transtracheal ventilation is ideal for emergency situations where there is a lack of time to intubate the patient or when a total airway obstruction is present.

Figure 1A:
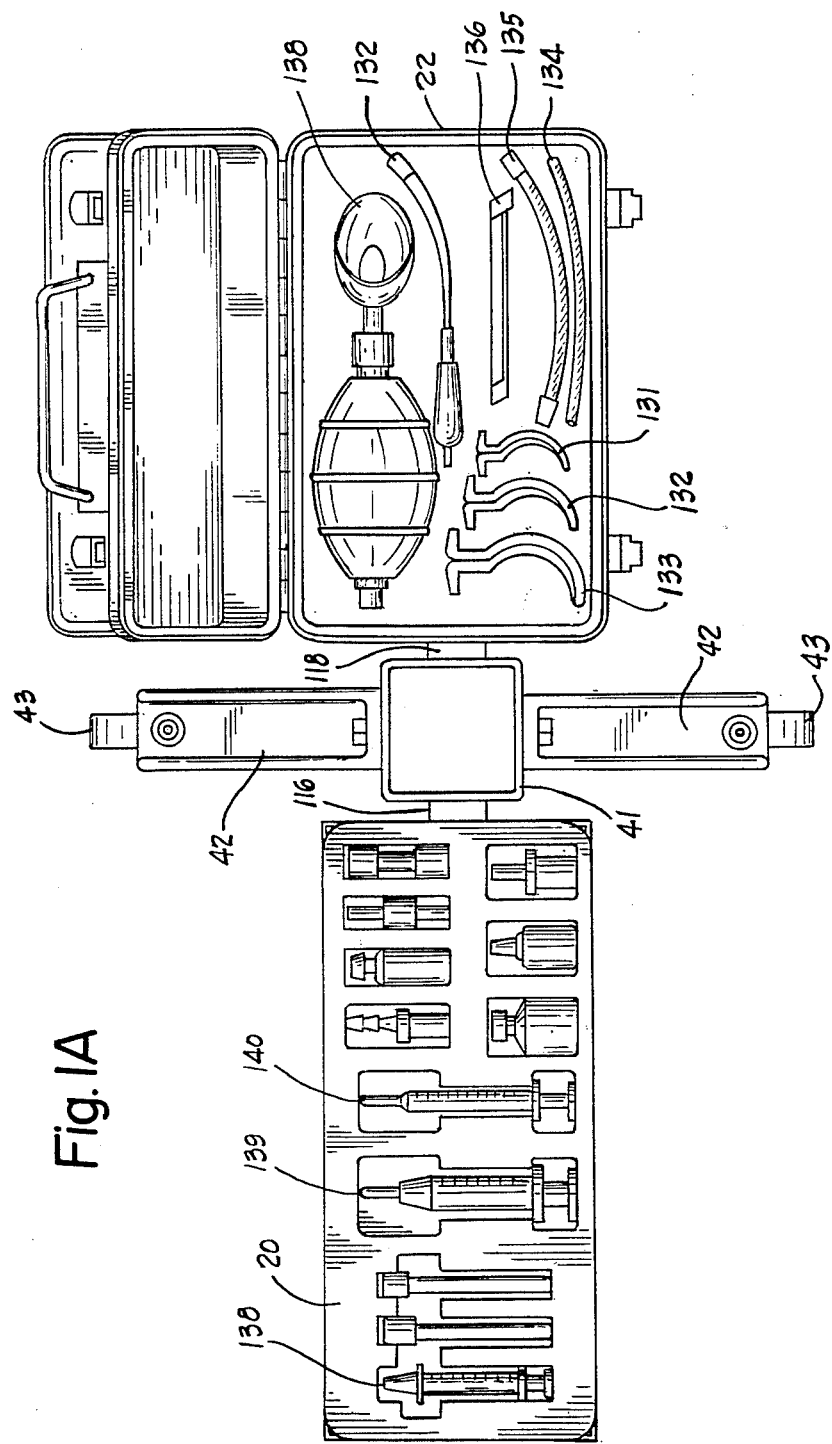
FIG. 1A is a top plan view of the supporting stand with two storage containers shown in a generally horizontal orientation.

The jet ventilation device 120 includes a flexible tube 121 with a jet ventilation gun 122 at one end and a jet needle valve 123 at the other end. A large bore needle (12 or 14 gauge) 124 is connected to the jet ventilation device 120 via a Luer lock 125. The jet ventilation gun 122 has a trigger 126 to deliver blasts of oxygen through the jet needle valve 123. Alternatively, the jet ventilation device 120 with attached jet ventilation gun 125 may be connected to an oropharyngeal airway 131, 132, 133, illustrated in FIG. 1A, via the jet needle valve 122.

The second oxygen regulator 18 supplies oxygen at high pressure to the jet ventilation device 120 through flexible tubing 28. The second regulator 18 regulates oxygen flow via an adjustable handle 36. A third gauge 38 indicates the pressure from the oxygen canister 14b. The pressure of oxygen delivered to the patient is indicated by a fourth gauge 40. Jet ventilation is accomplished by pressing the trigger 126 on the gun 122 to release blasts of oxygen as needed.

Thus, in a single hand held unit, which is hand holdable for easy transport with the patient, a physician or other medical emergency person can administer oxygen in a way best suited for a patient's needs.

Figure 2:
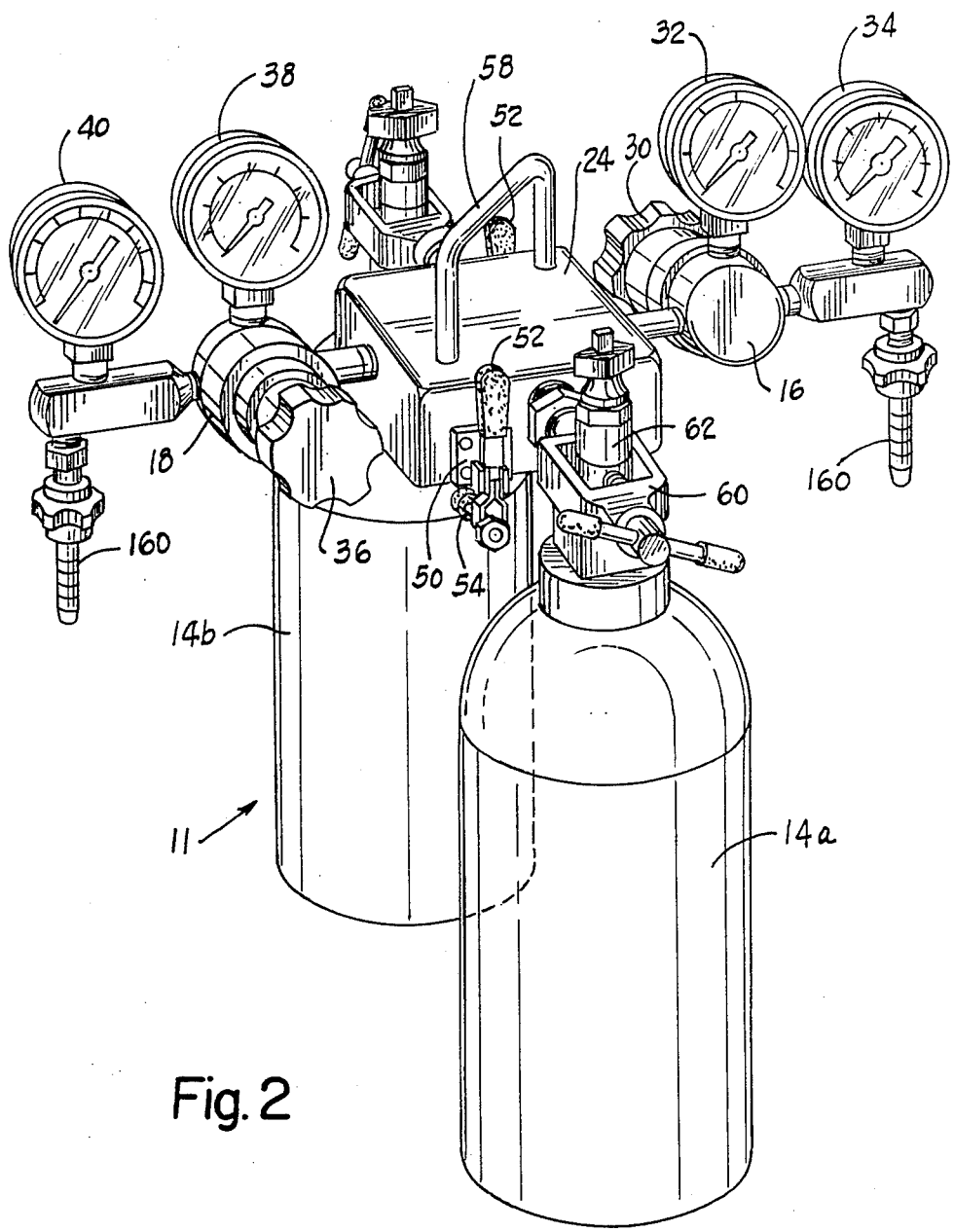
FIG. 2 is a perspective view or an enlarged scale as compared with FIG. 1 of the mobile resuscitating unit which normally is a portion of the apparatus, the view showing two oxygen bottles and a manifold for delivering oxygen to a patient through control valves coupled to the manifold.

The moveable stand 12 (FIG. 1) includes a three inch steel tubing vertical support 41 approximately 29½ inches in length. Four legs 42 are welded to the support 41. Casters 43 mounted to the legs 42 engage the floor to allow the unit 10 to be maneuvered out of storage and into the vicinity of the patient. This construction results in a very sturdy unit which is not susceptible to tipping or unsteady movement. The manifold 24 engages a top most portion of the support 41 and is held in place by two clamps 50 which are actuated by levers 52 (FIG. 2) to cause rounded elastomeric plungers 54 to frictionally engage opposite sides of the support 41. To lift the unit 11 from the stand 12, the levers 52 are manually released to disengage the contacts 54 to allow the manifold 12 and accompanying canisters 14a, 14b to be carried by a handle 58.

Figure 4:
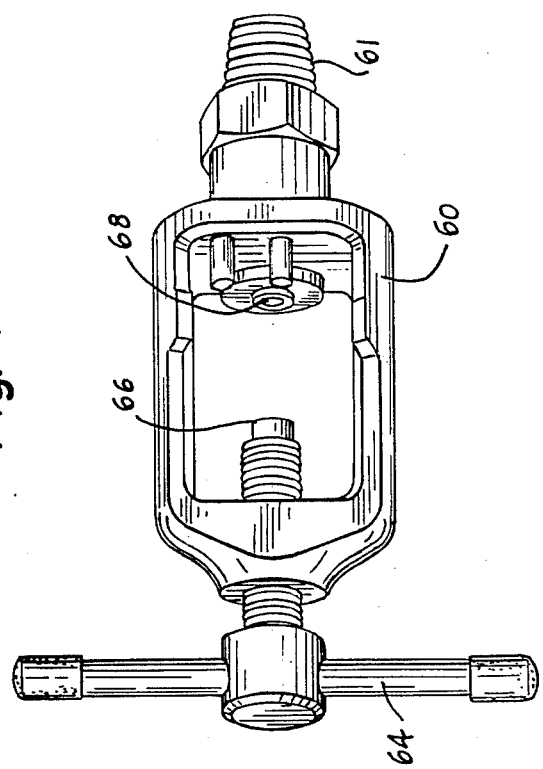
FIG. 4 is a perspective view of a connector for coupling an oxygen bottle to the manifold.

The oxygen canisters 14a, 14b are preferably aluminum weighing less than corresponding steel canisters. A full canister of the preferred size contains 240 liters of high pressure oxygen. The canister is coupled to the manifold 24 by a yoke 60 (FIG. 4) having a tapered threaded connector 61 which engages the manifold 24. To connect the oxygen canister 14 to the manifold 24, a user slips an oxygen canister coupling 62 through the yoke 60 and tightens a yoke handle 64 causing a plunger 66 to engage the canister coupling 62. Continued rotation of the yoke handle 64 forces a canister valve against a yoke valve seat 68 to route oxygen through the valve seat 68 to the manifold 24.

Figure 7:
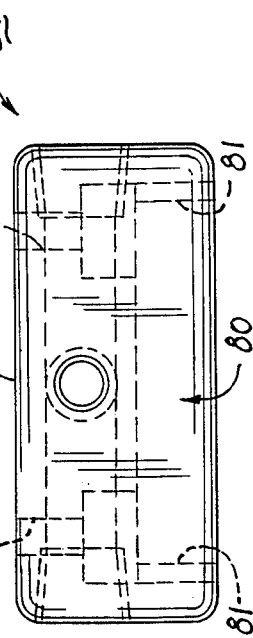
FIGS. 5–7 are top plan, front elevational, and side elevational views of the manifold.
Figure 5:
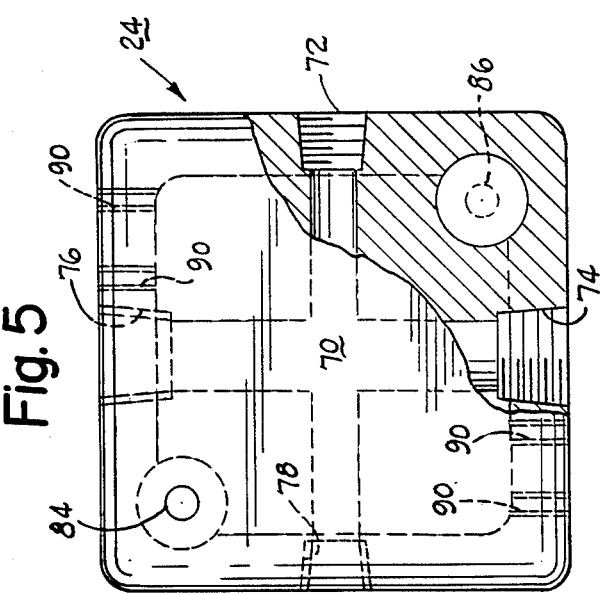
Figure 6:
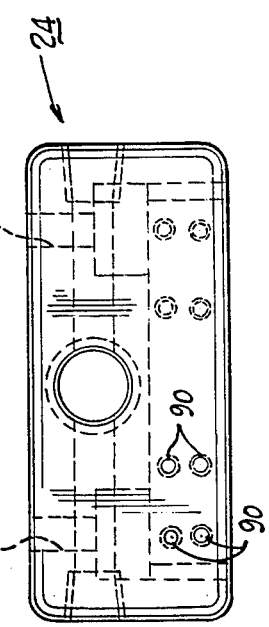

The preferred construction of the manifold is shown in FIGS. 5–7. The manifold 24 defines a throughpassage 70 having two oxygen inlets 72, 74 and two outlets 76, 78. The two inlets 72, 74 are coupled to the oxygen canisters 14 via passageways in the two yokes 60 supporting those canisters. The outlets 76, 78 are threaded to accommodate correspondingly threaded connectors of the oxygen regulators 16, 18.

The manifold 24 defines a box-like structure having a hollow cavity 80 extending approximatley ⅓ of the way through the thickness of the manifold. The cavity defines inner walls 81 which engage the support 41 when the moveable unit 11 is mounted on the stand 12. A top manifold surface 82 defines two apertures 84, 86 which receive the manifold handle 58. Two ends of the handle 58 are threaded and are secured to the manifold by a washer and nut which are secured to the threaded ends of the handle 58 from a bottom of the manifold.

The two clamps 50 are connected to the manifold 24 by connectors which extend through apertures 90 (FIG. 5) on either side of the manifold 24. In a disclosed and preferred arrangement, the two clamps 50 are bolted to the manifold 24. When supported on the stand 12, the manifold cavity 80 fits over the square end of the stand 12. The two clamps 50 are then actuated so that the clamp plungers 54 engage the stand to secure the oxygen delivery unit 11 in place.

Similar clamps 141 are used to support and lock in place the two storage containers 20, 22 in their horizontal orientation. The containers are each supported by a pivotally mounted arm 142, 144 (FIG. 1) supported by rigid horizontal supports 143, 145 extending from the support 41. The two clamps 140 lock the arms in a horizontal position (FIG. 1) to facilitate medical personnel using resuscitating implements stored within the containers 20, 22. When not in use, two locking levers 146, 148 are rotated away from the stand allowing the storage containers 20, 22 to pivot away from the horizontal orientation into a vertical orientation which substantially reduces the amount of space taken up by the combined oxygen delivery unit 11 and stand 12 when not in use.

Since it is anticipated the resuscitating unit 10 will be typically utilized in an emergency situation, the tube 26 leading from the control valves 16, 18 is stored for immediate access. This is also true for the oxygen mask 28. As seen most clearly in FIG. 1, directly beneath the oxygen canisters 14a, 14b horizontally extending rods 150 and knobs 152 are connected to the vertical stand at convenient locations for storing the tube 26 and mask 28. When an emergency arises, the mask and tube can be quickly unwound from the stand, attached to an appropriate one of the two valves and positioned over the patient's face as the user opens one or the other of the valves and adjusts oxygen flow to the patient.

The two oxygen regulators 16, 18 are commercially available from Western Equipment. The volume regulator 16 is Model No. M1-540-FGH and the pressure regulator 18 is Model No. M1-540-PG. In addition to the indicators and dials mentioned above each regulator includes a nozzle connector 160 to which the tubing 28 is secured.

In addition to the oropharyngeal airways 131, 132, 133 the container 22 may be equipped with endotracheal tubes 134, 135, 136, an aspirator attachment 137, and a self-inflating bag and mask 138. The container 20 typically has syringes 138, 139, 140 to deliver drugs such as epinephrine for acute allergic reactions; diazepam for convulsions; antihistamines, such as chlorpheniramine or diphenhydramine, for delayed allergic responses; analgesics such as meperidine or morphine for the acute pain of myocardial infarction; and vasopressors, such as methoxamine, for hypotension associated with acute adrenal insufficiency or drug overdose reaction. Other useful items are breakable ampules of ammonia or amyl nitrate, and oral bronchodialators.

Many variations and modifications of the invention will be apparent to those skilled in the art from the above detailed description. Therefore, it is to be understood that, within the scope of the appended claims, the invention can be practiced otherwise than as specifically shown and described.

I claim:

1. A portable resuscitating apparatus comprising:
  a mobile support stand which can be maneuvered;
  a storage container attached to the stand for storing patient resuscitating equipment;
  a manifold body mounted on the stand, said manifold body defining a mounting surface to engage the stand and further defining a first output port and a second output port in fluid communicating with an oxygen delivery conduit in said body coupled to at least one oxygen inlet port for routing oxygen through said oxygen delivery conduit;
  a handle attached to the manifold;
  first and second flow control means coupled to said first and second output ports on said manifold, said first flow control means having a first valve and a manual adjusting means for controlling a pressure of oxygen routed to a patient and said second flow control means having a second valve and a manual adjusting means for controlling a volume per unit time of oxygen to a patient, each of said first and second flow control means further having an output nozzle;
  a pressurized oxygen source connected to the manifold for routing oxygen through the oxygen inlet port through the oxygen delivery conduit to the first and second flow control means;
  routing means coupleable to the nozzle of one of said first and second flow control means for directing pressurized oxygen to a patient; and
  a release mechanism coupled to the manifold having friction means for frictionally engaging the stand and means for releasing the friction means from engagement with the stand to allow the manifold, flow control means, oxygen source and routing means to be disconnected from the stand and carried via the handle.

2. The portable unit of claim 1 wherein the storage container is moveably connected to the stand so that when not in use said container can be moved from a use to a storage orientation to reduce the space required to store said resuscitating unit.

3. A portable resuscitating apparatus comprising:
  a moveable support stand which can be maneuvered in relation to a patient and including an upright support member;
  a storage container attached to the stand for storing patient resuscitating equipment, the storage container being moveably mounted on the stand so that the container can be moved from an in use orientation to a storage orientation to reduce the space required to store said resuscitating apparatus;
  a manifold structure mounted on the stand comprising:
    (i) a box-like body having a top surface, a bottom surface and four-side surfaces; said body defining a throughpassage for routing oxygen from an oxygen inlet port on one side surface to first and second oxygen output ports on two other side surfaces;
    (ii) a handle coupled to the top surface for carrying the body structure; and
    (iii) release means coupled to opposite side surfaces of the body structure and including pivoting friction means for engaging the upright support member of the movable support stand to secure said manifold to the movable support stand;
    (iv) said bottom surface defining a recess that extends into the body structure to receive a supporting portion of said upright support member;
  first and second flow control means coupled to the first and second oxygen output ports of the manifold and each of said first and second flow control means having a manual control for manually adjusting fluid flow, said first flow control means including a first valve for controlling oxygen pressure and said second flow control means having a second valve for controlling oxygen volume with each valve having a nipple;
  a pressurized oxygen source connected to the manifold for supplying oxygen through the manifold oxygen inlet port through the throughpassage to the first and second flow control means, said source including one or more pressurized oxygen container coupleable to said manifold for delivering oxygen to the first valve for controlling oxygen pressure and to the second valve for controlling oxygen volume;

routing means connected to the flow control means for directing pressurized oxygen from a selected one of the first and second valves to a patient; and said release means for detachably connecting the manifold to the stand to allow the manifold, flow control means, oxygen source and routing means to be disconnected from the stand and carried via the manifold handle.

4. A portable resuscitating apparatus comprising a movable support stand which can be maneuvered in relation to a patient;

one or more mask holders attached to the stand for holding oxygen masks;

one or more spindles attached to the stand adapted to hold flexible tubing in the coiled position;

two storage containers attached to the stand for storing patient resuscitating equipment, the storage containers being movably mounted on the stand so that the containers can be moved from a use position to a storage position, at least one of said storage containers comprising a latchable case adapted to hold the equipment within the container in a storage position;

a manifold mounted on the stand defining two oxygen inlet ports and a passageway leading to two oxygen outlet ports;

a handle connected to the manifold to facilitate detaching the manifold from the stand;

two pressurized oxygen sources connected to the two manifold inlet ports;

a volume regulator connected to one manifold outlet port for regulating the volume of oxygen dispensed by a selected one of the oxygen sources, said volume regulator including a first oxygen source contents gauge coupled to a first oxygen flow gauge calibrated to deliver oxygen at up to 15 liters per minute, said first oxygen flow gauge being coupled to a first nipple;

a pressure regulator connected to a second manifold outlet port for regulating the pressure of oxygen dispensed by a selected one of the oxygen sources, said pressure regulator including a second oxygen source contents gauge coupled to a second oxygen flow gauge calibrated to deliver oxygen at up to 100 psi, said second oxygen flow gauge being coupled to a second nipple;

routing means coupleable to a selected one of the first and second nipples comprising flexible hosing for routing oxygen from a selected one of the two pressurized oxygen sources to a patient; and a release mechanism coupled to the manifold for detachably connecting the manifold tot he stand to allow the manifold, the two pressurized oxygen sources, the volume and pressure regulators and the routing means to be detached from the stand and carried via the handle.

5. A portable oxygen delivery unit for delivering oxygen at high pressure for jet ventilation and at low pressure for volume ventilation including;

a manifold comprising
  (i) a box-like body structure having a top surface, a bottom surface and four-side surfaces; said body structure defining a throughpassage for routing oxygen from an oxygen inlet port on one side surface to first and second oxygen output ports on other side surfaces;
  (ii) a handle coupled to the top surface for carrying the body structure; and
  (iii) release means coupled to opposite sides of the body structure and including pivoting friction means for engaging a movable stand to support said manifold;
  (iv) said bottom surface defining a recess that extends into the body structure to receive a supporting portion of said moveable stand;

a first flow control means coupled to the manifold for receipt of oxygen from said first output port and second flow control means coupled to the manifold for receipt of oxygen from said second output port;

each of said flow control means having a control for manually adjusting fluid flow, said first flow control means including a first valve for controlling oxygen pressure to deliver oxygen at high pressure for jet ventilation and second second flow control means having a second valve for controlling oxygen volume per unit time to deliver oxygen at a low pressure for volume ventilation, with each valve having an output nozzle;

a pressure oxygen source coupled to the oxygen inlet port of said manifold for supplying oxygen through the manifold to the flow control means; and routing means connected to one of said first and second flow control means for directing pressurized oxygen from a selected one of the first and second valves to a patient.

* * * * *